United States Patent
Rust et al.

[11] Patent Number: 6,050,942
[45] Date of Patent: Apr. 18, 2000

[54] DIGITAL SCANLINE SIGNAL PROCESSOR FOR AN ULTRASONIC DIAGNOSTIC IMAGING SYSTEM

[75] Inventors: David W. Rust, Seattle; Robert H. Pedersen, Woodinville; David N. Roundhill, Bothell, all of Wash.

[73] Assignee: ATL Ultrasound, Bothell, Wash.

[21] Appl. No.: 08/893,426

[22] Filed: Jul. 11, 1997

[51] Int. Cl.[7] ........................................... A61B 8/00
[52] U.S. Cl. ................................................. 600/437
[58] Field of Search ............................. 600/455, 454, 600/456, 449, 443

[56] References Cited

U.S. PATENT DOCUMENTS

| | | | |
|---|---|---|---|
| 5,152,292 | 10/1992 | Karp | 600/455 |
| 5,409,007 | 4/1995 | Saunders et al. | 600/454 |
| 5,482,045 | 1/1996 | Rust et al. | 600/454 |
| 5,515,852 | 5/1996 | Karp et al. | 600/455 |
| 5,544,655 | 8/1996 | Diagle | 600/443 |
| 5,634,465 | 6/1997 | Schmiesing et al. | 600/454 |
| 5,891,038 | 4/1999 | Seyed-Bolorforosh et al. | 600/447 |

*Primary Examiner*—Marvin M. Lateef
*Assistant Examiner*—Maulin Patel
*Attorney, Agent, or Firm*—W. Brinton Yorks, Jr.

[57] ABSTRACT

A digital scanline signal processor which processes beamformed echo signals includes a normalization circuit, a speckle reduction processor, and a gain stage which amplifies detected echo signals. The normalization circuit applies depth dependent gain to the scanline signals to equalize the amplitudes in channels of the processor with different passband characteristics. A log compression circuit includes two compression functions for low level and high level echo signals.

20 Claims, 4 Drawing Sheets

DIGITAL SCANLINE SIGNAL PROCESSOR FOR AN ULTRASONIC DIAGNOSTIC IMAGING SYSTEM

This invention relates to ultrasonic diagnostic imaging systems and, in particular, to the processing of digital scanline echo signals in an ultrasonic diagnostic imaging system.

Ultrasound systems which operate with array transducers employ beamformers to form scanlines from the echo signals of the individual elements of the array. Once each scanline has been formed, it may then be processed to form a B mode (two dimensional or 2D) image, an M-mode (time motion mode) display, or a colorflow image. In conventional ultrasound systems, the scanline signals will be amplitude detected and compressed to form a 2D image or an M-mode display, or will be accumulated with other scanline signals in an ensemble for Doppler signal estimation. The Doppler signals (velocity or variance) may then be combined with 2D echo signals to form a colorflow display.

In the course of such processing the scanline signals can be subjected to additional processing to enhance the echo information. For instance, the echo signals can be processed to compensate for aberrations caused by the tissue through which the echoes have passed or artifacts created by the manner in which the echoes have been processed in the ultrasound system. A significant enhancement which may also be employed is speckle reduction, as described in U.S. Pat. No. 4,561,019 (reissued as U.S. Pat. No. Re 35,148). Speckle arises due to the constructive and destructive interference of scattered coherent echoes as they return from the tissue of the body. The '019 patent performs speckle reduction by separating a broadband echo signal into discrete frequency bands of coherent echo signals, separately detecting the coherent signals in each band to form noncoherent signals, then combining the noncoherent echo signals. The speckle pattern of each detected band is uncorrelated, and is reduced when the noncoherent echo components are combined. It is desirable to perform speckle reduction as well as other image enhancements in a processor which processes ultrasonic scanline signals.

In accordance with the principles of the present invention, a digital multi-channel scanline signal processor is provided which performs a variety of signal enhancements, including speckle reduction, time gain control, bandpass filtering, normalization for varying aperture effects, synthetic aperture formation, scanline interpolation, log compression, the formation of multizone scanlines, and lowpass filtering. By combining a number of these functions the processor can be produced in a highly integrated I.C. form with the versatility to process different types of echo information (2D, Doppler) in rapid succession and even simultaneously.

Figure 1:
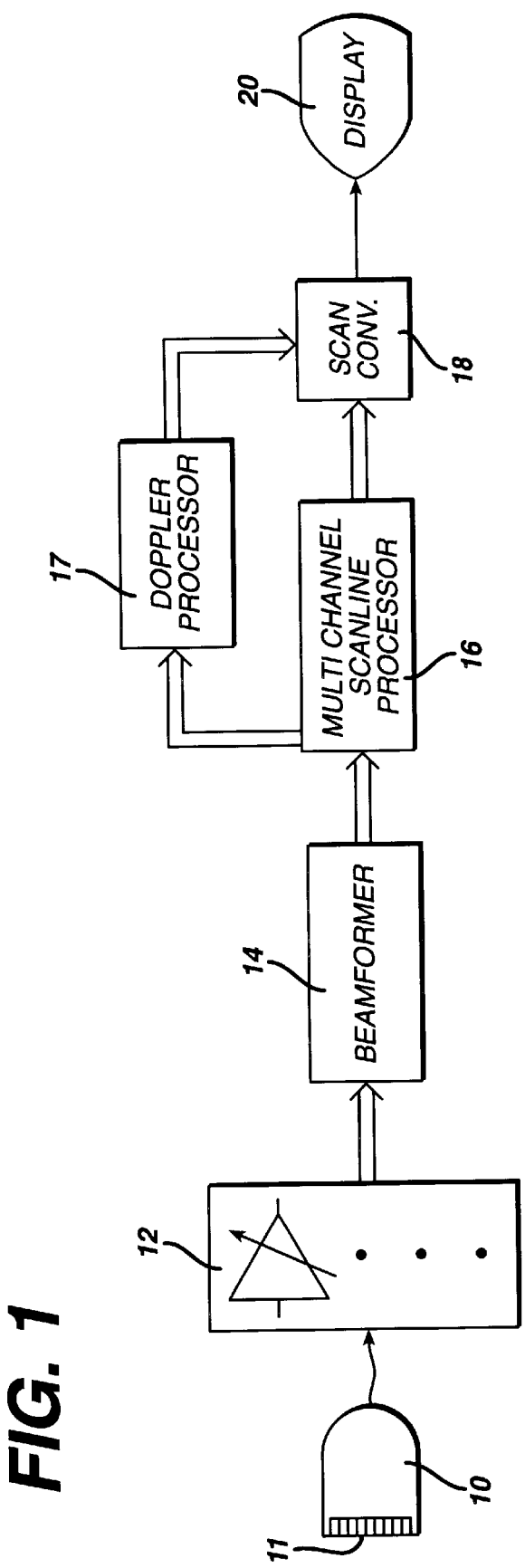
FIG. 1 illustrates in block diagram form an ultrasonic diagnostic imaging system constructed in accordance with the present invention.

Referring first to FIG. 1, an ultrasonic diagnostic imaging system constructed in accordance with the present invention is shown in block diagram form. A scanhead 10 includes an array transducer 11 comprising a plurality of individual transducer elements. These transducer elements are coupled to processing channels of a beamformer 14 by means of separate time gain control (TGC) amplifiers 12. In the preferred embodiment the beamformer 14 is a digital beamformer. Each echo signal received from a TGC amplifier is digitized by an analog to digital converter (ADC) at the input to each beamformer channel. Each beamformer channel then appropriately delays its received echo signal and the delayed echo signals from all of the elements are then combined to form a coherent RF (radio frequency) scanline echo signal.

The scanline signals are coupled to a multi-channel scanline processor 16, which processes the scanline signals for 2D, M-mode, spectral Doppler or colorflow imaging as described below. The processed scanline signals are coupled to a scan converter 18 for formation of image data in the desired image format. For colorflow or spectral Doppler display the processed scanline signals are coupled to the scan converter by way of a Doppler processor 17, which produces velocity, variance, or power Doppler signals. The scan converted image signals are coupled to a video processor (not shown) and thence to an image display 20 for display.

Figure 2:
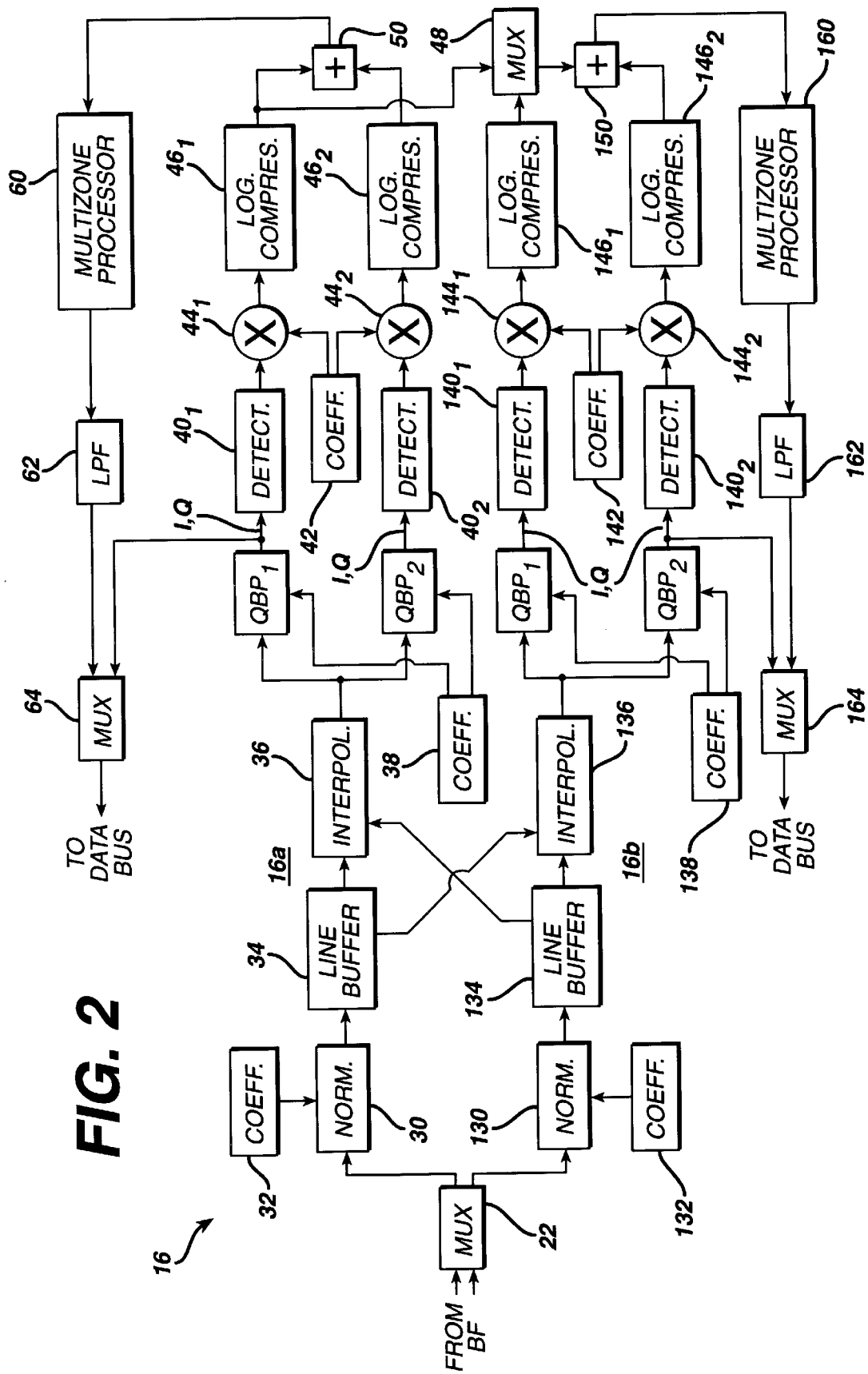
FIG. 2 illustrates in block diagram form a digital multi-channel scanline signal processor constructed in accordance with the principles of the present invention.

A multi-channel scanline processor 16, constructed in accordance with the principles of the present invention, is shown in block diagram form in FIG. 2. The signal and data lines connecting the blocks of the block diagram all represent multi-conductor digital data paths, as the scanline processor of the illustrated embodiment is entirely digital. Scanline echo data from the beamformer 14 is applied to a multiplexer 22. When the beamformer produces only a single scanline at a time or scanline data in a time interleaved format, only a single digital data path is needed between the beamformer and the multiplexer 22. In the illustrated embodiment, two digital data paths are shown, enabling two simultaneously generated scanlines to be coupled to the scanline processor 16 in parallel.

The operation of the scanline processor 16 when receiving a single scanline will first be described. The initial data words of the scanline are headers which tell the scanline processor how scanline data is to be received from the beamformer and how it is to be processed. The multiplexer 22 applies the scanline echo data following the headers in parallel to the two channels 16a,16b of the scanline processor illustrated in FIG. 2. Each channel of the scanline processor has a normalization stage 30,130 which multiplies the scanline data by a scale factor on a sample by sample basis to produce gain or attenuation that can vary with depth. The scale factor for each channel is provided by normalization coefficients stored in or generated by coefficient circuits 32,132, which in a preferred embodiment are digital memories. As the multiplying coefficients are changed along the sequence of scanline echoes, depth dependent gain or attenuation is produced.

The function of the normalization stages is two-fold. One is to compensate for a transducer aperture which expands with depth of scan. As signals from an increasing number of transducer are used with increasing depth, the magnitude of the summed beamformed signals will increase. This increase is offset by reduced gain (increased attenuation) in the normalization stage, in proportion to the rate at which channels are added to the beamforming process, so that the resultant echo sequence will be unaffected by the changing aperture.

Figure 3B:
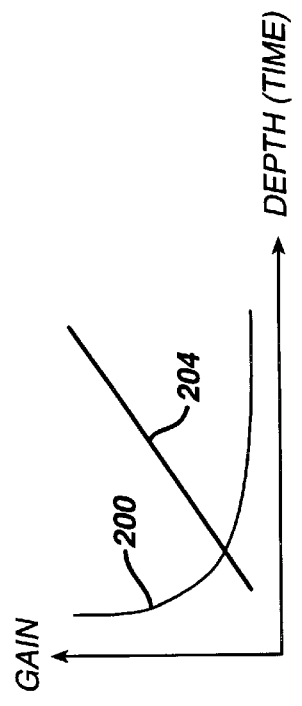
FIGS. 3a and 3b illustrate combined normalization and time gain control characteristics for two channels of the scanline signal processor of FIG. 2.
Figure 3A:
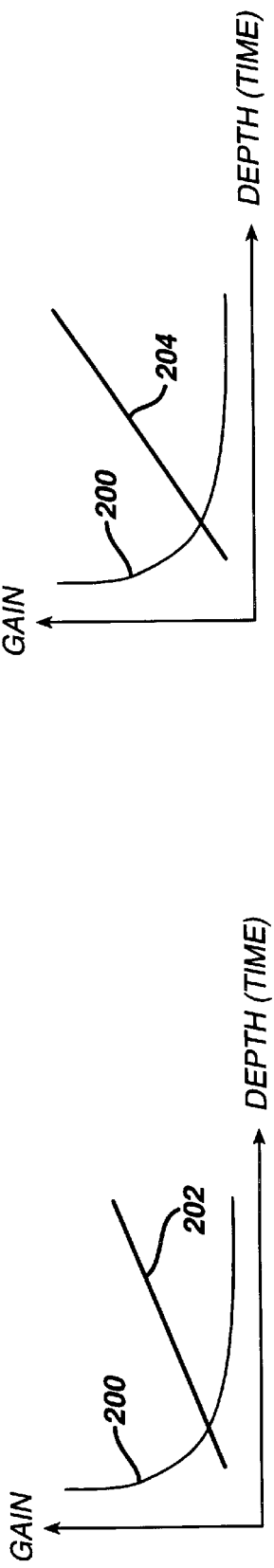
Figure 4:
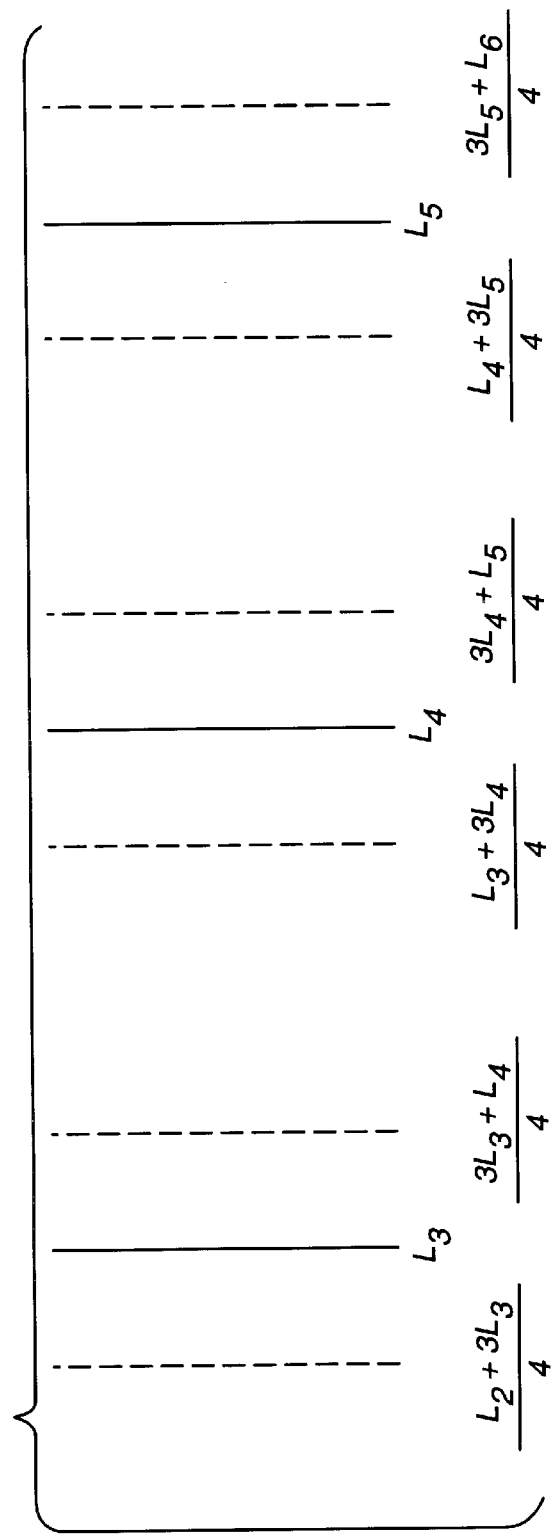
FIG. 4 illustrates a pattern of interpolated scanlines produced by a preferred embodiment of the scanline signal processor of the present invention.

The second function of the normalization stages is to equalize the nominal signal amplitudes of the two channels when frequency compounding is employed. The nominal signal amplitudes of the multiple passbands used for frequency compounding are desirably the same, so that the original relative signal levels will be preserved after the passbands are summed to restore the original broad passband. But ultrasound signals are subject to depth dependent attenuation which varies with frequency, higher frequencies being more greatly attenuated with depth than lower frequencies. To account for this depth dependent attenuation the coefficients provide signal gain which increases with depth. Since frequency compounding employs different frequency passbands in the two channels of the scanline processor 16, the depth dependent gain of the two channels differs from one channel to the other. In particular, the rate of gain increase for the higher frequency passband channel is greater than that of the lower frequency passband channel. This is illustrated in FIGS. 3a and 3b, which illustrate the normalization gain characteristics of the two channels. The normalization gain of each channel exhibits a depth dependent characteristic 200 as shown in FIGS. 3a and 3b. This decreasing gain characteristic offsets the effect of an increasing aperture in each channel. The channel which will provide the low frequency passband for frequency compounding also has a depth dependent gain characteristic as shown by gain curve 202 in FIG. 3a. The high frequency passband channel has a more rapidly increasing depth dependent gain characteristic as shown by gain curve 204 in FIG. 3b. Each depth dependent gain characteristic is chosen to offset the effect of depth dependent gain for the particular frequency passband used by that channel for frequency compounding. Since higher frequencies suffer more rapid attenuation with depth than lower frequencies, the gain curve 204 for the high frequency passband is steeper than that for the low frequency passband.

In a preferred embodiment the coefficients of the coefficient circuits apply a gain or attenuation characteristic which is a combination of the two characteristics 200,202 or 200,204. Preferably, the coefficient memories 32,132 store multiple combined gain curves which are changed with memory addressing to match scanhead characteristics or the type of signals being processed (2D or Doppler). The rate of gain change may be controlled by the rate at which the coefficients are changed for the multiplier of each normalization stage 30,130.

After processing by the normalization stages 30,130, the echo signals in each channel 16a,16b are coupled to line buffers 34,134. The line buffers perform two functions. First, each line buffer stores the first half aperture beamformed echo signals for synthetic aperture formation. The stored first half aperture signals are combined with the second half aperture signals as the latter are produced to form echo signals from the full synthetic aperture.

Second, the line buffers 34,134 each store a preceding scanline when the interpolators 36,136 are operating to interpolate scanline data from consecutively received scanlines. Each of the interpolators 36,136 interpolates additional scanline data between two received scanlines. In a preferred embodiment two interpolated scanlines are formed between each pair of received scanlines as described in U.S. patent application Ser. No. 08/800,005. The two interpolated scanlines are of the form $0.75L_n+0.25L_{n+1}$ and $0.25L_n+0.75L_{n+1}$, where $L_n$ and $L_{n+1}$ are consecutively received scanlines. The two interpolated scanlines are located at ¼ and ¾ of the distance from one received scanline to the next. In a preferred embodiment, as described in the aforementioned patent application, each weighted echo sample is saved so that it can be used in the formation of two interpolated scanlines. This results in a reversal of the sequence of interpolated scanline production from one pair of received scanlines to the next. In the preferred embodiment the 0.25 or 0.75 scaling factors are provided by the multipliers of the normalization stages. Stored weighted scanline signals are cross coupled from the line buffer of one channel to the interpolator of the other channel so that the two interpolated scanlines can be produced in unison, one at the output of each interpolator.

Figure 5:
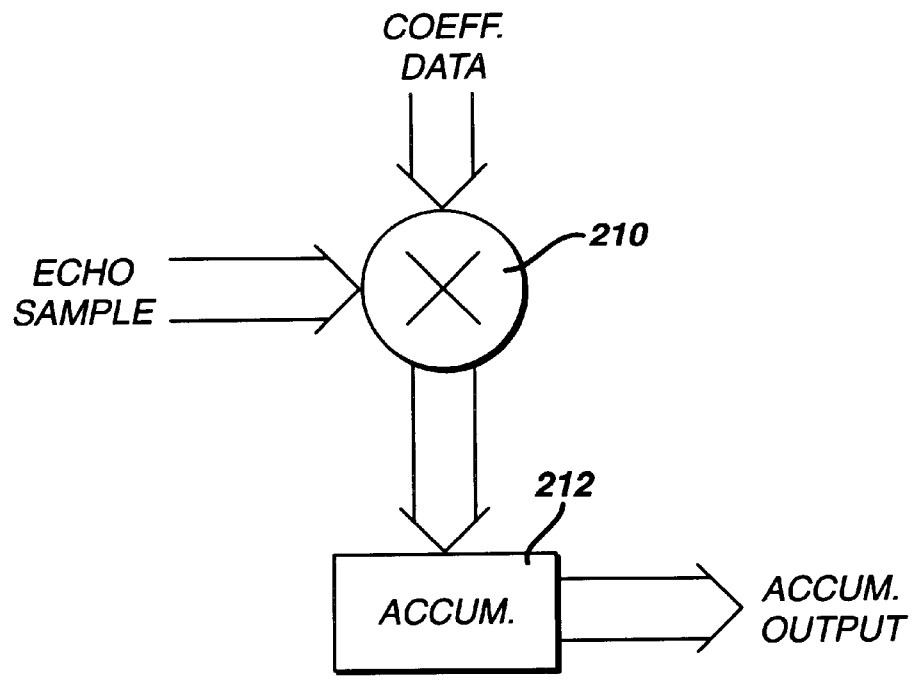
FIG. 5 is a block diagram of one of the multiplier accumulators used in the filters of the processor of FIG. 2.

In the case where the interpolators 36,136 are not active and the scanline processor 16 is processing one scanline at a time, the same sequence of scanline echoes is produced at the output of each interpolator, varying only by the different time varying gain factors of the normalization stages of the respective channels 16a, 16b. The echo signals in each channel are next coupled to quadrature bandpass filters (QBPs) in each channel. The quadrature bandpass filters provide three functions: band limiting the RF scanline data, producing in-phase and quadrature pairs of scanline data, and decimating the digital sample rate. Each QBP comprises two separate filters, one producing in-phase samples (I) and the other producing quadrature samples (Q), with each filter being formed by a plurality of multiplier-accumulators (MACs) implementing an FIR filter. One such MAC is shown in FIG. 5. As an echo sample of the scanline data is applied to one input of a digital multiplier 210 a coefficient is applied to the other multiplier input. The product of the echo sample and the weighting coefficient is stored in an accumulator 212 where it may be accumulated with previous products. Other MACs receive the echo samples at different phases and likewise accumulate weighted echo samples. The accumulated outputs of several MACs can be combined, and the final accumulated product comprises filtered echo data. The rate at which accumulated outputs are taken sets the decimation rate of the filter. The length of the filter is a product of the decimation rate and the number of MACs used to form the filter, which determine the number of incoming echo samples used to produce the accumulated output signal. The filter characteristic is determined by the values of the multiplying coefficients. Different sets of coefficients for different filter functions are stored in coefficient memories 38,138, which are coupled to apply selected coefficients to the multipliers of the MACs.

The coefficients for the MACs which form the I filter implement a sine function, while the coefficients for the Q filter implement a cosine function. For frequency compounding, the coefficients of the active QBPs additionally implement a sync function multiplied by a sine wave at the center frequency of the desired passband. In the instant case, when the scanline processor 16 is operating on only a single scanline at a time, $QBP_1$ in channel 16a is producing I and Q samples of the scanline data in a first, low frequency passband, and $QBP_2$ in channel 16b is producing I and Q samples of the scanline data in a second, higher frequency passband. Thus, the spectrum of the original broadband echo signals is divided into a high frequency band and a low frequency band. To complete the frequency compounding process, the echo data in the passband produced by $QBP_1$ of channel 16a is detected by a detector $40_1$ and the detected signals are coupled to one input of a summer 150. In a preferred embodiment detection is performed digitally by implementing the algorithm $(I^2+Q^2)^{1/2}$. The echo data in the complementary passband produced by QBP$_2$ of channel 16b is detected by a detector 140$_2$ and these detected signals are coupled to a second input of the summer 150. When the signals of the two passbands are combined by the summer 150, the uncorrelated speckle effects of the two passbands will cancel, reducing the speckle artifacts in the 2D image created from the signals.

Each of the two channels is seen to include two QBPs, labeled QBP$_1$ and QBP$_2$ in each channel. These QBPs each begin a split of the respective channel into two subchannels, denoted by the subscripts 1 and 2 in each channel. The subchannels accommodate frequency compounding when the beamformer 14 is producing multiple simultaneous scanlines or the interpolators 36,136 are each producing an interpolated scanline at the same time. In those instances, the data of the scanline being processed in channel 16a is separated into two passbands by QBP$_1$ and QBP$_2$ of channel 16a, the signals of the two passbands are detected by detectors 40$_1$,40$_2$, then combined by summer 50 to produce a speckle reduced scanline at the output of summer 50. Channel 16b operates in a similar manner on the scanline data in that channel, using QBP$_1$ and QBP$_2$ of channel 16b to separate the scanline data into two passbands, detecting the signals in detectors 140$_1$,140$_2$, then combining the detected data to produce a second speckle reduced scanline at the output of summer 150.

Following the detector in each subchannel is a gain stage formed by multipliers 44$_1$,44$_2$,144$_1$,144$_2$ which receive weighting coefficients from coefficient memories 42,142. The purpose of this gain stage is to partition the balance of analog and digital gains in the ultrasound system for optimal system performance. Some of the gains in the echo signal path may be automatically implemented by the ultrasound system, while others, such as the manual gain control and the TGC gain of TGC amplifiers 12, may be controlled by the user. The system partitions these gains so that the analog gains preceding the ADCs of the beamformer are adjusted optimally for the dynamic input range of the ADCs. The digital gain is adjusted to optimize the brightness of the image. The two gains together implement gain control changes effected by the user.

In the preferred embodiment the gain imparted to the scanline signals by the multipliers 44$_1$,44$_2$,144$_1$, 144$_2$ is selected in concert with the gain of the preceding normalization stage 30,130 in the channel. The gain of each normalization stage is chosen to prevent the attainment of saturation levels in the QBPs, as may occur when strong signals from contrast agents or harmonic imaging are being received. To prevent saturation levels the maximum gain of the normalization stage is controlled, and any reduction imposed by reason of this control is restored by the gain of the succeeding multiplier 44$_1$,44$_2$,144$_1$,144$_2$.

The gain function provided by these multipliers could be performed anywhere along the digital signal processing path. It could be implemented by changing the slope of the compression curves discussed below. It could also, for instance, be performed in conjunction with the gains applied by the normalization stages. This implementation, however, would eliminate the ability to effect saturation control discussed above. The present inventors have found implementation of this gain function to be eased when provided after detection, and in the preferred embodiment by use of a multiplier after detection.

The signals produced by the gain stages 44$_1$,44$_2$, 144$_1$, 144$_2$ generally exhibit a greater dynamic range than the display 20. Consequently, the scanline signals of the multipliers are compressed to a suitable dynamic range by lookup tables. Generally the compression is logarithmic, as indicated by log compression processors 46$_1$,46$_2$,146$_1$,146$_2$. The output of each lookup table is proportional to the log of the signal input value. These lookup table are programmable so as to provide the ability to vary the compression curves, and the brightness and dynamic range of the scanline signals sent on for display.

Figure 6:
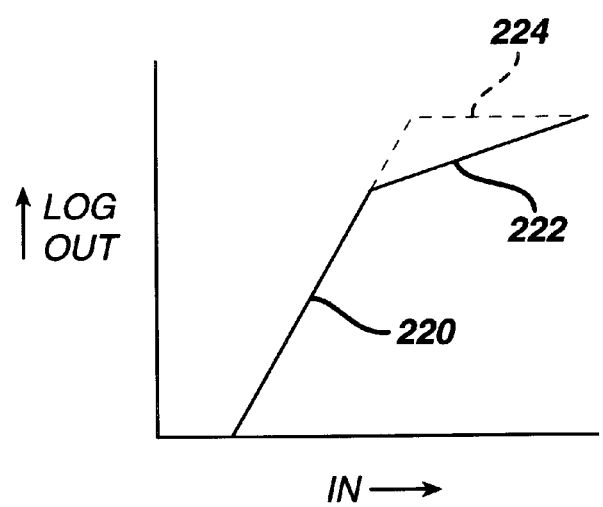
FIG. 6 illustrates the transfer characteristic of the log compression processor of a preferred embodiment of the present invention.

Conventionally log compression processors implement a single compression curve to scale the dynamic range of the echo data. However the present inventors have found this to be disadvantageous when a bright object is in the image area adjacent to an object of interest with lesser brightness. For example, a user may want to examine the liver where it is adjacent to the diaphragm of the body. Since the muscle tissue of the diaphragm is a strong reflector of ultrasound echoes, the diaphragm will appear considerably brighter than the adjacent liver tissue, and may even reach a saturation brightness level. To reduce the brightness of the diaphragm the user may turn down the gain to reduce maximum brightness in the image, but this will also reduce the contrast in the liver. The present inventors have overcome this dilemma by implementing a dual function or dual slope compression curve, as illustrated in FIG. 6. As this graph shows, very low noise input signals produce no output signal. Above the noise threshold, the input signals are compressed in accordance with a first compression curve 220. Above a selected level the input signals are compressed in accordance with a second compression function. The conventional compression curve would only exhibit a single function, as indicated by the dashed continuation of the curve 220 to a dashed saturation level 224. In the foregoing example, the echoes from the liver would exhibit the dynamic range provided by the first curve 220, and the diaphragm echoes would be scaled by the second curve 222, rather than attaining the saturation level 224.

As discussed above, when each channel 16a,16b is processing a separate scanline, compressed, speckle reduced scanline signals are produced at the outputs of summer 50,150 of the two channels. When the two channels are each processing one passband of the same scanline, a multiplexer 48 couples the signals from the passband formed by QBP$_1$ of channel 16a to summer 150, where the signals are combined with those of the passband formed by QBP$_2$ of channel 16b. When frequency compounding is not active, the detected and compressed broadband echo signals simply pass through the summers without alteration, or may bypass the summers altogether.

The outputs of the summers 50,150 are coupled to multizone processors 60,160, where multizone focused scanlines may be formed when this function is selected by the user. The multizone processors store scanline segments from the current transmit focal zone during multizone operation, and as different transmit focal zone segments are received, the multizone processors assemble the segments to form a complete scanline over the depth of interest. The segments can be received in any depth order, with deepest to shallowest being preferred for reduction of artifacts from prior transmit pulses. As the final segment of each scanline is received, the multizone processor sends the full scanline to a lowpass filter 62,162. These lowpass filters, like the QBPs, are formed by combinations of multiplier-accumulators with variable coefficients, arranged to implement FIR filters, to control the filter characteristic. The lowpass filters provide two functions. One is to smooth the boundaries between scanline segments when multizone operation is employed. A second function is to match the scanline data rate to the vertical line density of the display 20, so as to prevent aliasing in the displayed image. The FIR filters perform this function by selectively decimating or interpolating the scanline data.

The processed scanline data is then put onto a data bus for subsequent process such as scan conversion, and display. A multiplexer 64,164 at the output of each channel puts scanline data onto the data bus, and can select data from several points in the process for the bus. When the scanline data is to be Doppler processed, the I and Q values produced by the QBPs are put on the data bus for receipt by the Doppler processor 17. Scanline data for 2D display is taken from the lowpass filters 62,162 and put on the bus by the multiplexer. The multiplexer puts the scanline data onto the bus in accordance with the protocol used to negotiate the bus. The multiplexer also adds header data to the beginning of the scanline to identify the scanline data for subsequent processors.

It will be appreciated that a constructed embodiment of a scanline processor of the present invention may employ more than two channels. Two two-channel processors may be employed, each with an inputs coupled to receive a separate contemporaneous scanline from a beamformer producing multiple simultaneous scanlines. It will also be appreciated that more than two passbands can be used for frequency compounding; for instance, three or more passbands may be employed. It will further be appreciated that the order of the functions in a constructed embodiment may be different from the order shown in the preferred embodiment, depending on implementation and other considerations. By virtue of its all digital, highly integratable nature, the scanline processor of the present invention readily lends itself to such architectural modifications and expansions.

What is claimed is:

1. An ultrasonic diagnostic imaging system comprising:
   a multiline beamformer for producing signals of at least two coherent scanlines in response to one transmit interval; and
   a speckle reduction circuit coupled to receive said coherent scanline signals from said multiline beamformer, for reducing the speckle content of said scanline signals.

2. The ultrasonic diagnostic imaging system of claim 1, wherein said speckle reduction circuit comprises a frequency compounding circuit.

3. An ultrasonic diagnostic imaging system, including a beamformer for producing signals of coherent scanlines, comprising:
   a normalization circuit for compensating for the effects of different apertures during the reception of echo signals;
   a multiple channel scanline processing circuit for processing said scanlines with different response characteristics;
   a processor for equalizing the nominal signal amplitudes of said multiple channels; and
   means for combining said differently processed scanlines.

4. The ultrasonic diagnostic imaging system of claim 3, wherein said equalizing processor comprises a depth dependent processor.

5. The ultrasonic diagnostic imaging system of claim 4, wherein said depth dependent processor comprises a time gain control circuit.

6. The ultrasonic diagnostic imaging system of claim 4, wherein said depth dependent processor applies different gain versus depth characteristics to different ones of said multiple channels.

7. An ultrasonic diagnostic imaging system, including a beamformer for producing signals of coherent scanlines, comprising:
   an interpolator responsive to said coherent scanline signals for producing coherent interpolated scanline signals; and
   a speckle reduction circuit coupled to receive said interpolated scanline signals, for reducing the speckle content of said signals.

8. An ultrasonic diagnostic imaging system, including a beamformer for producing signals of coherent scanlines, comprising:
   an interpolator responsive to said coherent scanline signals for producing interpolated scanline signals; and
   a speckle reduction circuit coupled to receive said interpolated scanline signals, for reducing the speckle content of said signals,
   wherein said beamformer comprises a multiline beamformer.

9. The ultrasonic diagnostic imaging system of claim 7, wherein said interpolator includes a line buffer.

10. An ultrasonic diagnostic imaging system, including a beamformer for producing signals of coherent scanlines, comprising:
    an interpolator responsive to said coherent scanline signals for producing interpolated scanline signals; and
    a speckle reduction circuit coupled to receive said interpolated scanline signals, for reducing the speckle content of said signals,
    wherein said interpolator includes a line buffer, and
    wherein said line buffer is further used to form a synthetic aperture.

11. An ultrasonic diagnostic imaging system, including a beamformer for producing signals of coherent scanlines, comprising:
    a normalization circuit for compensating for the effects of different apertures during the reception of echo signals;
    a detector for detecting normalized scanline signals; and
    a gain stage coupled to the output of said detector,
    wherein said gain stage applies a gain which has been partitioned between said normalization circuit and said gain stage.

12. The ultrasonic diagnostic imaging system of claim 11, wherein the gain of said normalization circuit is controlled to prevent the attainment of undesired saturation levels during processing between said normalization circuit and said gain stage.

13. An ultrasonic diagnostic imaging system, including analog circuitry which amplifies received ultrasonic echo signals and a beamformer coupled to receive said ultrasonic echo signals for producing signals of coherent scanlines, comprising:
    a detector for detecting said scanline signals; and
    a gain stage coupled to the output of said detector,
    wherein said beamformer comprises a digital beamformer;
    wherein the gain of said analog circuitry is chosen in consideration of the dynamic range of said digital beamformer; and
    wherein said gain stage applies a gain which is selected in consideration of the gain of said analog circuitry.

14. The ultrasonic diagnostic imaging system of claim 13, wherein said analog circuitry includes TGC circuitry.

15. The ultrasonic diagnostic imaging system of claim 13, wherein said digital beamformer includes a plurality of analog to digital converters, each exhibiting a given dynamic range.

16. The ultrasonic diagnostic imaging system of claim 13, wherein the gain of said gain stage is chosen in consideration of the brightness of an ultrasonic image.

17. An ultrasonic diagnostic imaging system, including a beamformer coupled to receive said ultrasonic echo signals for producing signals of coherent scanlines, comprising:

a detector for detecting said scanline signals; and a log compression circuit coupled to receive detected scanline signals, wherein said log compression circuit exhibits at least two compression characteristics.

18. The ultrasonic diagnostic imaging system of claim 12, wherein said log compression circuit exhibits a first compression function for low level echo signals, and a second compression function for high level echo signals.

19. The ultrasonic diagnostic imaging system of claim 1, wherein said coherent scanline signals are applied to said speckle reduction circuit over parallel digital paths.

20. The ultrasonic diagnostic imaging system of claim 1, wherein said coherent scanline signals are applied to said speckle reduction circuit in a time interleaved format.

* * * * *